(12) United States Patent
Sirinyan et al.

(10) Patent No.: US 7,728,011 B2
(45) Date of Patent: *Jun. 1, 2010

(54) DERMALLY APPLICABLE LIQUID FORMULATIONS FOR CONTROLLING PARASITIC INSECTS ON ANIMALS

(75) Inventors: Kirkor Sirinyan, Bergisch Gladbach (DE); Hubert Dorn, Wuppertal (DE); Martin Gilges, Koeln (DE); Olaf Hansen, Leichlingen (DE)

(73) Assignee: Bayer Animal Health GmbH (DE)

( * ) Notice: Subject to any disclaimer, the term of this patent is extended or adjusted under 35 U.S.C. 154(b) by 1383 days.

This patent is subject to a terminal disclaimer.

(21) Appl. No.: 10/682,127

(22) Filed: Oct. 9, 2003

(65) Prior Publication Data

US 2004/0161441 A1 Aug. 19, 2004
US 2009/0017084 A9 Jan. 15, 2009

Related U.S. Application Data

(63) Continuation of application No. PCT/EP02/03619, filed on Apr. 2, 2002.

(51) Int. Cl.
*A01N 43/40* (2006.01)

(52) U.S. Cl. ............... 514/341; 424/405; 514/351; 514/531

(58) Field of Classification Search .......... None
See application file for complete search history.

(56) References Cited

U.S. PATENT DOCUMENTS

| | | | |
|---|---|---|---|
| 4,590,272 A | 5/1986 | Shiokawa et al. | 544/335 |
| 4,647,570 A | 3/1987 | Shiokawa et al. | 514/341 |
| 4,742,060 A | 5/1988 | Shiokawa et al. | 514/252 |
| 4,772,620 A | 9/1988 | Shiokawa et al. | 514/341 |
| 4,774,247 A | 9/1988 | Shiokawa et al. | 514/256 |
| 4,806,553 A | 2/1989 | Shiokawa et al. | 514/332 |
| 4,849,432 A | 7/1989 | Shiokawa et al. | 514/341 |
| 4,882,344 A | 11/1989 | Shiokawa et al. | 514/342 |
| 4,914,113 A | 4/1990 | Shiokawa et al. | 514/333 |
| 4,918,086 A | 4/1990 | Gsell | 514/351 |
| 4,918,088 A | 4/1990 | Gsell | 514/357 |
| 4,948,798 A | 8/1990 | Gsell | 514/275 |
| 4,963,572 A | 10/1990 | Gsell | 514/357 |
| 4,963,574 A | 10/1990 | Bachmann et al. | 514/357 |
| 4,988,696 A | 1/1991 | Andrews et al. | |
| 5,034,404 A | 7/1991 | Uneme et al. | 514/365 |
| 5,034,524 A | 7/1991 | Shiokawa et al. | 544/124 |
| 5,039,686 A | 8/1991 | Davies et al. | 514/341 |
| 5,074,252 A | 12/1991 | Morgan, Jr. | 119/156 |
| 5,236,954 A | 8/1993 | Gladney et al. | 514/531 |
| 5,253,182 A | 10/1993 | Suzuki | 364/489 |
| 5,435,992 A | 7/1995 | Audegond et al. | 514/419 |
| 6,001,858 A | 12/1999 | Sirinyan et al. | |
| 6,033,731 A | 3/2000 | Liebert et al. | 427/244 |
| 6,080,796 A | 6/2000 | Liebert et al. | 521/64 |
| 6,232,328 B1 | 5/2001 | Dorn et al. | 514/341 |
| 7,384,938 B2 | 6/2008 | Sirinyan et al. | |
| 2002/0103233 A1* | 8/2002 | Arther | 514/341 |
| 2003/0055089 A1 | 3/2003 | Sirinyan et al. | 514/341 |

FOREIGN PATENT DOCUMENTS

| | | |
|---|---|---|
| AU | 633883 | 2/1993 |
| CN | 1176052 A | 3/1998 |
| CN | 1234181 A | 11/1999 |
| CN | 1236547 A | 12/1999 |
| DE | 3639877 | 11/1986 |
| DE | 3712307 | 4/1987 |
| EP | 135956 | 8/1984 |
| EP | 189972 | 1/1986 |
| EP | 302389 | 7/1988 |
| EP | 364844 | 10/1989 |
| EP | 368565 | 11/1989 |
| EP | 375907 | 11/1989 |
| EP | 383091 | 1/1990 |
| EP | 425978 | 10/1990 |
| EP | 428941 | 11/1990 |
| EP | 455000 | 4/1991 |
| EP | 461962 | 6/1991 |
| EP | 464830 | 7/1991 |
| EP | 471372 | 8/1991 |
| EP | 682869 | 5/1995 |
| EP | 976328 | 7/1999 |
| EP | 981955 | 8/1999 |
| FR | 2784011 | 10/1998 |
| JP | 63-287764 | 5/1987 |
| JP | 63-307857 | 6/1987 |
| JP | 2-207083 | 2/1989 |
| JP | 3-220176 | 1/1990 |
| JP | 3-279359 | 3/1990 |
| JP | 3-255072 | 5/1990 |

(Continued)

OTHER PUBLICATIONS

Calumpang, et al., Applicator Exposure to Imidacloprid while Spraying Mangoes, Bull. Environ. Contam. Toxicol., Nov. 1996, vol. 57, pp. 697-704.

(Continued)

*Primary Examiner*—Neil Levy

(57) ABSTRACT

The present invention relates to novel skin-friendly dermally applicable liquid formulations comprising permethrin and agonists or antagonists of nicotinic acetylcholine receptors of insects for controlling parasitic insects on animals.

4 Claims, No Drawings

FOREIGN PATENT DOCUMENTS

| | | |
|---|---|---|
| JP | 7-89803 | 9/1993 |
| JP | 7-247203 | 3/1994 |
| JP | 11-079917 | 3/1999 |
| RU | 2127517 C1 | 3/1999 |
| RU | 2130259 C1 | 5/1999 |
| WO | WO 91/17659 | 11/1991 |
| WO | WO 95/17090 | 6/1995 |
| WO | WO 96/17520 | 6/1996 |
| WO | WO 00/54591 | 9/2000 |
| WO | WO 02/43494 | 6/2002 |

OTHER PUBLICATIONS

Wamhoff, et al., Photodegradation of Imidacloprid, Journal of Agricultural and Food Chemistry, Apr. 1999, vol. 47, No. 4, pp. 1730-1734.

Toda, et al., Toxic Effect of Pesticides on the Larvae of *Chrysperla camea*, Proc. Assoc. Pl. Prot. Kyushu, 1997, vol. 43, pp. 101-105.

Zheng et al., Kinetics and Mechanism of the hydrolysis of Imidacloprid, Pesticide Science, Apr. 1999, vol. 55, No. 4, pp. 482-485.

\* cited by examiner

DERMALLY APPLICABLE LIQUID FORMULATIONS FOR CONTROLLING PARASITIC INSECTS ON ANIMALS

The present invention relates to novel skin-friendly dermally applicable liquid formulations comprising permethrin and agonists or antagonists of nicotinic acetylcholine receptors of insects for controlling parasitic insects on animals.

The use of topical formulations comprising permethrin, i.e. (3-phenoxyphenyl)methyl 3-(2,2-dichloroethenyl)-2,2-dimethylcyclopropanecarboxylates [CAS No. 52645-53-1], for controlling parasitic insects on animals is known (cf., for example, WO 95/17 090, JP-07 247 203, EP-A-567 368, EP-A461 962, U.S. Pat. Nos. 5,236,954 and 5,074,252).

Agonists or antagonists of the nicotinic acetylcholine receptors of insects are known, for example are known from agonists or antagonists of the nicotinic acetylcholine receptors of insects, for example from the European Laid-Open Applications Nos. 464 830, 428 941, 425 978, 386 565, 383 091, 375 907, 364 844, 315 826, 259 738, 254 859, 235 725, 212 600, 192 060, 163 855, 154 178, 136 636, 303 570, 302 833, 306 696, 189 972, 455 000, 135 956, 471 372, 302 389; the German Laid-Open Applications Nos. 3 639 877, 3 712 307; the Japanese Laid-Open Publications Nos. 03 220 176, 02 207 083, 63 307 857, 63 287 764, 03 246 283, 04 9371, 03 279 359, 03 255 072; U.S. Pat. Nos. 5,034,524, 4,948,798, 4,918,086, 5,039,686, 5,034,404; PCT Applications Nos. WO 91/17 659, 92/4965; the French Application No. 2611 114; the Brazilian Application No. 88 03 621. Also known is the use of spot-on formulations comprising agonists or antagonists of nicotinic acetylcholine receptors of insects for controlling parasitic insects on animals (see, for example, WO 98/27 817, EP-A-682 869 and EP 0 976 328).

Combinations of permethrin with agonists or antagonists of nicotinic acetylcholine receptors of insects for controlling parasites have likewise already been described in the prior art (cf., for example, CN-1 245 637, WO 00/54 591, U.S. Pat. No. 6,080,796, EP-A-981 955, U.S. Pat. No. 6,033,731, JP-07 089 803).

The disadvantage of the permethrin-based spot-on formulations is the low activity against ticks and fleas.

In general, spot-on formulations based on agonists or antagonists of nicotinic acetylcholine receptors are highly active against fleas. However, they have the disadvantage that they are ineffective against ticks.

Unfortunately, the known combination formulations comprising permethrin and agonists or antagonists of nicotinic acetylcholine receptors are not particularly suitable for controlling parasites on animals, in particular pets. They require the use of relatively large amounts of active compound and, in many cases, cause skin irritations. Permethrin is a strongly aprotic compound, whereas agonists and antagonists of nicotinic acetylcholine receptors, in particular imidacloprid analogues, are protic compounds. Accordingly, it is not easy to find a dermally applicable liquid formulation which comprises both active compounds and has the following properties:

good solubility of the active compounds
skin-friendly
low toxicity
low skin penetration (since the action of the active compounds should preferably be non-systemic)
high efficacy.

For this reason, successful control of ticks and fleas hitherto required a treatment of the animals with both of the said spot-on formulations. For ecological and economic reasons, it is desirable to replace these formulations by formulations which are skin-friendly and toxicologically acceptable and which are furthermore distinguished by good long-term action of at least three to four weeks, especially against ticks and fleas, at a small applicable volume (for example 0.1 ml/1.0 kg [body weight of the animal to be treated]). Furthermore, such a formulation should, in all climate zones, be sufficiently storage-stable, usually for at least three years, for example in the conventional spot-on tubes.

Accordingly, it was an object of the present invention to provide an easy-to-use skin-friendly and environmentally friendly formulation for dermal application active against parasitic insects, in particular against ticks and fleas, which formulation comprises permethrin and agonists or antagonists of nicotinic acetylcholine receptors of insects.

This object is achieved by the compositions according to the invention described below.

The present invention relates to
1. compositions, comprising
a) 35-60% by weight of the active compound permethrin
b) 2.5-12.5% by weight of imidacloprid or an imidacloprid analogue
c) 27.5-62.5% by weight of N-methylpyrrolidone
d) 0-5% by weight of water
e) 0-0.5% by weight of phenolic antioxidants and
f) 0-0.5% by weight of organic acids.

The stated percentages by weight are based on the total weight.

According to a preferred embodiment, the compositions according to the invention additionally comprise
g) 2.5-10% by weight of cosolvent.

The compositions according to the invention are usually liquid and are suitable for dermal application, in particular as pour-on or spot-on formulations.

Surprisingly, the ectoparasiticidal activity of the compositions according to the invention comprising permethrin in combination with imidacloprid or an imidacloprid analogue is higher than would have been expected from the activities of the individual components. By using these compositions, it is therefore possible to reduce the application rates of active compound and to increase long-term action. As a result, their use has economic and ecological advantages.

The compositions according to the invention are highly suitable for use in controlling parasites.

Parasites which may be mentioned are:
from the order of the Anoplura e.g. *Haematopinus* spp., *Linognathus* spp., *Solenopotes* spp., *Pediculus* spp., *Pthirus* spp.;
from the order of the Mallophaga e.g. *Trimenopon* spp., *Menopon* spp., *Eomenacanthus* spp., *Menacanthus* spp., *Trichodectes* spp., *Felicola* spp., *Damalinea* spp., *Bovicola* spp.;
from the order of the Diptera e.g. *Aedes* spp., *Culex* spp., *Simulium* spp., *Phlebotomus* spp., *Chrysops* spp., *Tabanus* spp., *Musca* spp., *Hydrotaea* spp., *Muscina* spp., *Haematobosca* spp., *Haematobia* spp., *Stomoxys* spp., *Fannia* spp., *Glossina* spp., *Lucilia* spp., *Calliphora* spp., *Auchmero-myia* spp., *Cordylobia* spp., *Cochliomyia* spp., *Chrysomyia* spp., *Sarcophaga* spp., *Wohlfartia* spp., *Gasterophilus* spp., *Oesteromyia* spp., *Oedemagena* spp., *Hypoderma* spp., *Oestrus* spp., *Rhinoestrus* spp., *Melophagus* spp., *Hippobosca* spp.;
from the order of the Siphonaptera e.g. *Ctenocephalides* spp., *Echidnophaga* spp., *Ceratophyllus* spp., *Pulex* spp.;
from the order of the Metastigmata e.g. *Hyalomma* spp., *Rhipicephalus* spp., *Boophilus* spp., *Amblyomma* spp., *Haemaphysalis* spp., *Dermacentor* spp., *Ixodes* spp., *Argas* spp., *Ornithodorus* spp., *Otobius* spp.;

from the order of the Mesostigmata e.g. *Dermanyssus* spp., *Ornithonyssus* spp., *Pneumonyssus* spp.;

from the order of the Prostigmata e.g. *Cheyletiella* spp., *Psorergates* spp., *Myobia* spp., *Demodex* spp., *Neotrombicula* spp.;

from the order of the Astigmata e.g. *Acarus* spp., *Myocoptes* spp., *Psoroptes* spp., *Chorioptes* spp., *Otodectes* spp., *Sarcoptes* spp., *Notoedres* spp., *Knemidocoptes* spp., *Neoknemidocoptes* spp. *Cytodites* spp., *Laminosioptes* spp.

The compositions according to the invention are particularly suitable for controlling ectoparasites, preferably ticks and/or fleas, on animals, in particular warm-blooded animals. The compositions according to the invention are preferably used for pets. Here, pets are to be understood as including, in particular, dogs, cats and other warm-blooded animals of a size not greater than that of a dog; i.e. they have a body weight of generally not more than 90 kg, preferably not more than 50 kg. The compositions according to the invention are particularly preferably used for dogs and cats, in particular for dogs.

Since the treated animals generally also spread a certain amount of the composition used in the surroundings, for example by scratching or debris, the compositions according to the invention may act not only directly on the animal but, correspondingly, also in their surroundings.

To prepare the liquid formulations according to the invention, it is possible to use all customary isomer mixtures of the active permethrin compound. The preferred isomer mixture comprises 35-45% of cis- and 55-65% of trans-permethrin. The particularly preferred isomer mixture comprises 37.5-42.5% of cis- and 57.5-62.5% of trans-permethrin.

The amounts of permethrin in the composition according to the invention can be varied broadly between 35 and 60%. Preference is given to amounts in the range of 45-60%, and, with particular preference, the composition according to the invention comprises permethrin in the range of 47.5-55%.

Likewise, it is possible to vary the amounts of imidacloprid or imidacloprid analogue broadly between 2.5 and 12.5%, where preference is given to amounts in the range of 5.0-10.0%. With particular preference, imidacloprid or the imidacloprid analogue is used in the compositions according to the invention in amounts in the range of 7.5-10%.

Of course, said formulations may also comprise further suitable active compounds.

Examples which may be mentioned are growth-inhibiting active compounds and synergists, pyriproxyfen {2-[1-methyl-2-(4-phenoxyphenoxy)ethoxy]pyridine CAS No.: 95737-68-1}, methopren [(E,E)-1-methylethyl 11-methoxy-3,7,11-trimethyl-2, 4-dodecadieneoate, CAS No.: 40596-69-8] and triflumuron {2-chloro-N-[[[4-(tri-fluoromethyl)phenyl]amino]carbonyl]benzamide CAS No.: 64628-44-0}.

Agonists or antagonists of the nicotinic acetylcholine receptors of insects which may be mentioned as being preferred are imidacloprid analogues.

Imidacloprid analogues are to be understood as meaning compounds of the formula (I):

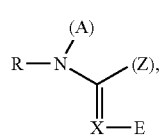
(I)

in which

R represents hydrogen or optionally substituted radicals from the group consisting of acyl, alkyl, aryl, aralkyl, heteroaryl and heteroarylalkyl;

A represents a monofunctional group from the group consisting of hydrogen, acyl, alkyl, aryl or represents a bifunctional group which is attached to the radical Z;

E represents an electron-withdrawing radical;

X represents the radicals —CH= or =N—, where the radical —CH= may be attached to the radical Z instead of a hydrogen atom;

Z represents a monofunctional group from the group consisting of alkyl, —O—R, —S—R,

or represents a bifunctional group which is attached to the radical A or the radical X.

Particular preference is given to compounds of the formula (I) in which the radicals are as defined below:

R represents hydrogen and also represents optionally substituted radicals from the group consisting of acyl, alkyl, aryl, aralkyl, heteroaryl, heteroarylalkyl.

Acyl radicals which may be mentioned are formyl, alkylcarbonyl, arylcarbonyl, alkylsulphonyl, arylsulphonyl, (alkyl)(aryl)phosphoryl, which for their part may be substituted.

Alkyl which may be mentioned is $C_{1-10}$-alkyl, in particular $C_{1-4}$-alkyl, specifically methyl, ethyl, isopropyl, sec- or tert-butyl, which for their part may be substituted.

Aryl which may be mentioned are phenyl and naphthyl, in particular phenyl.

Aralkyl which may be mentioned are phenylmethyl and phenethyl.

Heteroaryl which may be mentioned is heteroaryl having up to 10 ring atoms and, as heteroatoms, N, O and S, in particular N. Specific mention may be made of thienyl, furyl, thiazolyl, imidazolyl, pyridyl, benzothiazolyl.

Heteroarylalkyl which may be mentioned are heteroarylmethyl and heteroarylethyl having up to 6 ring atoms and, as heteroatoms, N, O, S, in particular N.

Exemplary and preferred substituents are:

alkyl having preferably 1 to 4, in particular 1 or 2, carbon atoms, such as methyl, ethyl, n- and isopropyl and n-, iso- and tert-butyl; alkoxy having preferably 1 to 4, in particular 1 or 2, carbon atoms, such as methoxy, ethoxy, n- and isopropyloxy and n-, iso- and tert-butyloxy; alkylthio having preferably 1 to 4, in particular 1 or 2, carbon atoms, such as methylthio, ethylthio, n- and isopropylthio and n-, iso- and tert-butylthio; haloalkyl having preferably 1 to 4, in particular 1 or 2, carbon atoms and preferably 1 to 5, in particular 1 to 3, halogen atoms, where the halogen atoms are identical or different and are preferably fluorine, chlorine or bromine, in particular fluorine, such as trifluoromethyl; hydroxyl; halogen, preferably fluorine, chlorine, bromine and iodine, in particular fluorine, chlorine and bromine; cyano; nitro; amino; monoalkyl- and dialkylamino having preferably 1 to 4, in particular 1 or 2, carbon atoms per alkyl group, such as methylamino, methylethylamino, n- and isopropylamino and methyl-n-butylamino; carboxyl; carbalkoxy having preferably 2 to 4, in particular 2 or 3, carbon atoms, such as carbomethoxy and carboethoxy;

sulpho (—SO₃H); alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl, and also heteroarylamino and heteroarylalkylamino, such as chloropyridylamino and chloropyridylmethylamino.

A particularly preferably represents hydrogen and also represents optionally substituted radicals from the group consisting of acyl, alkyl, aryl, which are preferably as defined under R. A furthermore represents a bifunctional group. Mention may be made of optionally substituted alkylene having 1-4, in particular 1-2, carbon atoms, substituents which may be mentioned being the substituents listed further above, where the alkylene groups may be interrupted by heteroatoms from the group consisting of N, O and S.

A and Z together with the atoms to which they are attached may form a saturated or unsaturated heterocyclic ring. The heterocyclic ring may contain a further 1 or 2 identical or different heteroatoms and/or hetero groups. Preferred heteroatoms are oxygen, sulphur or nitrogen and preferred hetero groups are N-alkyl, where the alkyl of the N-alkyl group contains preferably 1 to 4, in particular 1 or 2, carbon atoms. Alkyl which may be mentioned are methyl, ethyl, n- and isopropyl and n-, iso- and tert-butyl. The heterocyclic ring contains 5 to 7, preferably 5 or 6, ring members.

Examples of the heterocyclic ring which may be mentioned are pyrrolidine, piperidine, piperazine, hexamethyleneimine, hexahydro-1,3,5-triazine, morpholine, which may optionally be substituted, preferably by methyl.

E represents an electron-withdrawing radical, where mention may be made in particular of NO₂, CN, haloalkylcarbonyl, such as 1,5-halo-C₁₋₄-carbonyl, in particular COCF₃.

X represents —CH= or —N=.

Z represents optionally substituted radicals alkyl, —OR, —SR, —NRR, where R and the substituents preferably have the meaning given above.

Z can furthermore, in addition to the ring mentioned above, form, together with the atom to which it is attached and the radical

instead of X, a saturated or unsaturated heterocyclic ring. The heterocyclic ring may contain a further 1 or 2 identical or different heteroatoms and/or hetero groups. Preferred heteroatoms are oxygen, sulphur or nitrogen and preferred hetero groups are N-alkyl, where the alkyl or N-alkyl group contains preferably 1 to 4, in particular 1 or 2, carbon atoms. Alkyl which may be mentioned are methyl, ethyl, n- and isopropyl and n-, iso- and tert-butyl. The heterocyclic ring contains 5 to 7, preferably 5 or 6, ring members.

Examples of the heterocyclic ring which may be mentioned are pyrrolidine, piperidine, piperazine, hexamethyleneimine, morpholine and N-methyl-piperazine.

Compounds which can be used according to the invention with very particular preference are compounds of the general formulae (II) and (III):

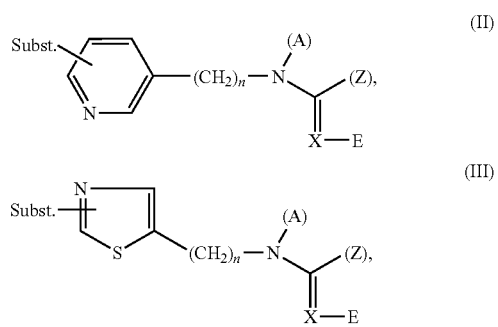

in which n represents 1 or 2,

Subst. represents one of the substitutents listed above, in particular halogen, very preferably chlorine, A, Z, X and E are as defined above.

The following particularly preferred compounds (imidacloprid and analogues) may be specifically mentioned:

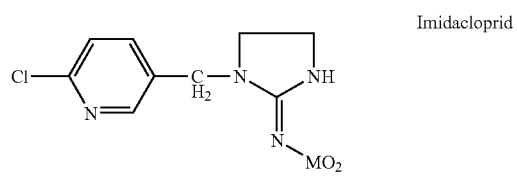

Imidacloprid

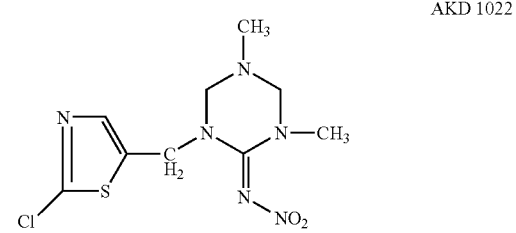

AKD 1022

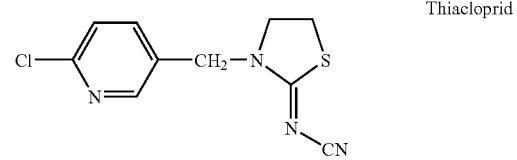

Thiacloprid

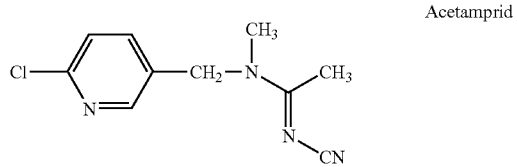

Acetamprid

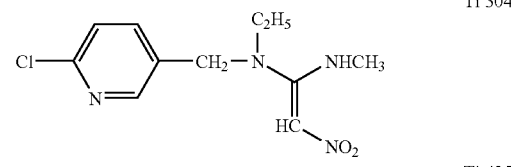

Ti 304

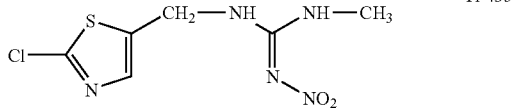

Ti 435

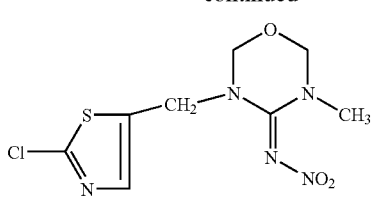
Thiamethoxam

The amount of N-methylpyrrolidone may be varied in the range of 27.5 to 62.5% by weight. Preferably it is from 35 to 50% by weight, particularly preferably from 40 to 45% by weight.

The amounts of antioxidant may be varied broadly in the range of 0-0.5%, where preference is given to amounts in the range of 0.05-0.25%. With particular preference, amounts in the range of 0.05-0.15% are used for preparing the compositions according to the invention. All customary antioxidants are suitable, preferably phenolic antioxidants, such as, for example, butylated hydroxytoluene, butylated hydroxyanisole, tocopherol.

The amount of organic acid may be varied broadly in the range of 0-0.5%, where preference is given to amounts in the range of 0.05-0.25%. With particular preference, amounts in the range of 0.05-0.15% are used for preparing the compositions according to the invention. Suitable for use in the compositions according to the invention are all pharmaceutically acceptable organic acids, in particular carboxylic acids, such as, for example, citric acid, tartaric acid, lactic acid, succinic acid and malic acid. Particular preference is given to the organic acids citric acid and malic acid. Very particular preference is given to citric acid. Their amount can be varied broadly, in particular in the range of 0.05 to 0.25%, where particular preference is again given to amounts in the range of 0.075-0.15%.

The amounts of cosolvent may be varied broadly in the range of 2.5-10% by weight, where preference is given to amounts in the range of 2.5-7.5% by weight. With particular preference, amounts in the range of 3.5-6.0% by weight are used in the compositions according to the invention.

Suitable cosolvents are organic solvents having a boiling point >80° C. and a flash point >75° C. The cosolvents preferably have a spreading action. In this context, reference may be made to relatively high-boiling aliphatic and also aromatic alcohols, aliphatic polyethers, aliphatic and/or aromatic esters and cyclic and/or acyclic carbonates.

However, for preparing the compositions according to the invention, preference is given to using aliphatic acyclic or cyclic ethers or polyethers and also fatty acid esters, in particular triglycerides.

Suitable for use in the compositions according to the invention are ethers or polyethers, for example from the group consisting of diethylene glycol monoethyl ether, dipropylene glycol monomethyl ether, tetrahydrofurfuryl alcohol and tetrahydrofurfuryl ethoxylate, where the two last-mentioned compounds are particularly preferred.

Fatty acid esters and triglycerides which may be mentioned are, for example:

isopropyl myristate, Miglyol 810, Miglyol 812, Miglyol 818, Miglyol 829, Miglyol 840 and Miglyol 8810 (for the definition of the miglyols see, for example, H. P. Fiedler, Lexikon der Hilfsstoffe für Pharmazie, Kosmetik und angrenzende Gebiete [Encyclopaedia of Auxiliaries for Pharmacy, Cosmetics and Related Fields], pages 1008-1009, Vol. 2, Publisher Cantor Verlag Aulendorf (1996)).

From the experiments carried out so far, it can be seen that the mixtures according to the invention modified with the cosolvents mentioned are distinguished by their better skin- and eye-friendliness, better biological activity and by their more favourable stability properties under cold conditions in the customary single-dose application tubes.

In addition to the components listed above, the compositions according to the invention may comprise further pharmaceutically acceptable auxiliaries. Auxiliaries which may be mentioned are, for example: spreaders and surfactants.

Spreaders are, for example, spreading oils, such as di-2-ethylhexyl adipate, isopropyl myristate, dipropylene glycol pelargonate, cyclic and acyclic silicone oils, such as dimethicone, and further co- and terpolymers thereof with ethylene oxide, propylene oxide and formaldehyde, fatty acid esters, triglycerides, fatty alcohols.

Surfactants which may be mentioned are: nonionic surfactants, for example polyethoxylated castor oil, polyethoxylated sorbitan monooleate, sorbitan monostearate, glycerol monostearate, polyoxyethyl stearate, alkylphenol polyglycol ethers;

ampholytic surfactants, such as di-Na N-lauryl-β-imino-dipropionate or lecithin;

anionic surfactants, such as Na lauryl sulphate, fatty alcohol ether sulphates, mono/dialkyl polyglycol ether orthophosphoric acid ester monoethanolamnine salt;

cationic surfactants, such as cetyltrimethylammonium chloride.

The compositions according to the invention can be prepared by customary processes, for example by mixing the active compounds with stirring with the other components and preparing a solution. The solution may, if appropriate, be filtered. Suitable containers are, for example, plastic tubes.

The liquid formulations according to the invention are distinguished by their excellent storage stability of at least three years in all climate zones. Owing to the high efficacy, the application volume may be kept small. Preferred application volumes are 0.075-0.25 ml/1.0 kg [body weight of the pet to be treated], preferably 0.1-0.15 ml/1.0 kg [body weight of the pet to be treated].

The formulations are highly suitable for being filled into and sold in storage-critical containers, such as, for example, single dose polypropylene tubes having a wall thickness of 300-500 µm and a filling volume of 1.0-4.0 ml.

Moreover, the compositions according to the invention are highly skin-friendly and have low toxicity.

Finally, owing to their biological degradability, they are environmentally friendly.

EXAMPLES

Example 1

A homogeneous spot-on solution comprising 45 g permethrin comprising 40% cis and 60% trans isomers 10 g imidacloprid (1-[(6-chloro-3-pyridine)methyl]-N-nitro-2-imidazolidinium) from Bayer AG 44.8 g N-methylpyrrolidone 0.1 g citric acid 0.1 g BHT (butylated hydroxytoluene)

Example 2

A homogeneous spot-on solution comprising
45 g permethrin comprising 40% cis and 60% trans isomers
10 g imidacloprid
40.8 g N-methylpyrrolidone
    4.0 g water
    0.1 g citric acid
    0.1 g BHT

Example 3

A homogeneous spot-on solution comprising
45 g permethrin comprising 40% cis and 60% trans isomers
10 g Ti 435, Chlothianidine from Takeda AG
44.8 g N-methylpyrrolidone
    0.1 g citric acid
    0.1 g BHT

Example 4

A homogeneous spot-on solution comprising
45 g permethrin comprising 40% cis and 60% trans isomers
10 g Diacloden (thiamethoxam) from Novartis AG
44.8 g N-methylpyrrolidone
    0.1 g citric acid
    0.1 g BHT

Example 5

A homogeneous spot-on solution comprising
45 g permethrin comprising 40% cis and 60% trans isomers
7.5 g imidacloprid
43.3 g N-methylpyrrolidone
    4.0 g water
    0.1 g citric acid
    0.1 g BHT

Example 6

A homogeneous spot-on solution comprising
45 g permethrin comprising 40% cis and 60% trans isomers
10.0 g imidacloprid
38.3 g N-methylpyrrolidone
    4.0 g water
    0.1 g citric acid
    0.1 g BHT (butylated hydroxytoluene)

Example 7

A homogeneous spot-on solution comprising
47.5 g permethrin comprising 40% cis and 60% trans isomers
10 g imidacloprid
42.3 g N-methylpyrrolidone
    0.1 g citric acid
    0.1 g BHT

Example 8

A homogeneous spot-on solution comprising
45 g permethrin comprising 40% cis and 60% trans isomers
8 g imidacloprid
46.8 g N-methylpyrrolidone
    0.1 g lactic acid
    0.1 g BHT

Example 9

A homogeneous spot-on solution comprising
45 g permethrin comprising 40% cis and 60% trans isomers
8 g imidacloprid
46.8 g N-methylpyrrolidone
    0.1 g lactic acid
    0.1 g butylated hydroxyanisole

Example 10

A homogeneous spot-on solution comprising
45 g permethrin comprising 40% cis and 60% trans isomers
10 g imidacloprid (1-[(6-chloro-3-pyridinyl)methyl]-N-nitro-2-imidazolidinium) from Bayer AG
39.8 g N-methylpyrrolidone
    0.1 g citric acid
    0.1 g BHT (butylated hydroxytoluene)
    5.0 g Miglyol 812 from Sasol Germany GmbH. D-58453 Witten

Example 11

A homogeneous spot-on solution comprising
45 g permethrin comprising 40% cis and 60% trans isomers
10 g imidacloprid
35.8 g N-methylpyrrolidone
    4.0 g water
    0.1 g citric acid
    0.1 g BHT
    5.0 g Miglyol 840 from Sasol Germany GmbH. D-58453 Witten

Example 12

A homogeneous spot-on solution comprising
45 g permethrin comprising 40% cis and 60% trans isomers
10 g Ti 435, Chlothianidine from Takeda AG
39.8 g N-methylpyrrolidone
    0.1 g citric acid
    0.1 g BHT
    5.0 g tetrahydrofurfuryl alcohol

Example 13

A homogeneous spot-on solution comprising
45 g permethrin comprising 40% cis and 60% trans isomers
10 g Diacloden (thiamethoxam) from Novartis AG
39.8 g N-methylpyrrolidone
    0.1 g citric acid
    0.1 g BHT
    5.0 g tetrahydrofurfuryl ethoxylate

Example 14

A homogeneous spot-on solution comprising
45 g permethrin comprising 40% cis and 60% trans isomers
7.5 g imidacloprid
40.0 g N-methylpyrrolidone
    0.1 g citric acid
    0.1 g BHT
    3.3 g Miglyol 812

Example 15

A homogeneous spot-on solution comprising
47.5 g permethrin comprising 40% cis and 60% trans isomers
10.0 g imidacloprid
33.8 g N-methylpyrrolidone
4.0 g water
0.1 g citric acid
0.1 g BHT (butylated hydroxytoluene)
5.0 g Miglyol 812

Example 16

A homogeneous spot-on solution comprising
47.5 g permethrin comprising 40% cis and 60% trans isomers
10 g imidacloprid
34.3 g N-methylpyrrolidone
0.1 g citric acid
0.1 g BHT
4.0 g tetrahydrofurfuryl alcohol
4.0 g Miglyol 812

Example 17

A homogeneous spot-on solution comprising
45 g permethrin comprising 40% cis and 60% trans isomers
8 g imidacloprid
40.8 g N-methylpyrrolidone
0.1 g lactic acid
0.1 g BHT
6.0 g tetrahydrofurfuryl alcohol

Example 18

A homogeneous spot-on solution comprising
45 g permethrin comprising 40% cis and 60% trans isomers
8 g imidacloprid
42.8 g N-methylpyrrolidone
0.1 g lactic acid
0.1 g butylated hydroxyanisole
4.0 g diethylene glycol monoethyl ether A. Activity Against Fleas on Dogs

*Ctenocephalides felis*

On days −4 and −1, dogs are infested with about 100 adult unfed *Ctenocephalides felis* per dog. The fleas are placed on the neck of the animal.

On day 0, the success of the infestation on the dog is examined by checking the awake animal for fleas. The number of live fleas is noted.

After the fleas have been counted, the animals are treated. The dogs of the control group are not treated. The medicaments to be examined according to Examples 1 to 18 are administered to the animals dermally as a spot-on in an application rate of 0.1 ml/kg of body weight. The application is carried out once on day 0. Only animals that are clinically healthy are used.

On day 1, all dogs are examined for live fleas. The results are noted with the crude data.

On days 7, 14, 21 and 28, all dogs are reinfested with about 100 adult unfed *Ctenocephalides felis* per dog. In each case one day after the reinfestation, all dogs are checked for live fleas. The results are noted with the crude data.

A formulation is considered to be highly active if, on day 1 and in each case on the second day after reinfestation, an efficacy of >95% is found, and this action persists for at least 3-4 weeks.

The efficacy is calculated using a modified formula according to Abbott:

$$\text{Efficacy \%} = \frac{\emptyset \text{ number of fleas} - \emptyset \text{ number of fleas } TG}{\emptyset \text{ number of fleas } CG} \times 100$$

CG: Control group
TG: Treatment group

The medicaments of Formulation Examples 1 to 18, applied as a spot-on at a dosage of 0.1 ml/kg, were found to be highly effective against *Ctenocephalides felis*.

B. Efficacy Against Ticks (*Rhipicefalus sanguineus*) on Dogs

In each case on days −4 and −1, dogs are sedated using 2% Rompun® (Bayer AG, active compound: xylazine hydrochloride) (0.1 ml/kg of body weight). Once all dogs have been sedated (after about 10-15 minutes), they are transferred to transport boxes, and 50 *Rhipicefalus sanguineus* (25 ♀, 25 ♂) per dog are applied to the neck of the animal. After about 1½ hours, the animals are retransferred from the transport box into the cage.

On day 0, the success of the infestation on the dog is examined by checking the awake animal for ticks. An intensive search is carried out in the region of the head and the ears, including the folds of the ears, in the region of the neck, on the lower abdomen, on the lower breast, on the flank and in between the toes and the limbs. The number of sucking live ticks is noted. Dead ticks are removed.

After the ticks have been counted, the animals are treated. The dogs of the control group are not treated. The medicaments to be examined are administered to the animals dermally, as a spot-on. Application is carried out once on day 0. Only animals which are clinically healthy are used.

On day 1 and day 2, all dogs are checked for living and dead sucking ticks. The results are noted with the crude data. On day 2, all living and dead ticks are removed from the dog.

On days 7, 14, 21 and 28, all dogs are reinfested with in each case 50 *Rhipicefalus sanguineus* (25 ♀, 25 ♂) per dog. In each case one and two days after the reinfestation, all dogs are checked for living and dead sucking ticks. The results are noted with the crude data. On the second day after the reinfestation, all living and dead ticks are removed from the dog.

A formulation is considered to be highly active if, on day 2 and in each case on the second day after reinfestation, an efficacy of >90% is found, and this action persists for at least 3 weeks.

For calculating the efficacy, a modified formula according to Abbott is used:

$$\text{Efficacy \%} = \frac{\emptyset \text{ number of ticks } CG - \emptyset \text{ number of ticks } TG}{\emptyset \text{ number of ticks } CG} \times 100$$

CG: Control group
TG: Treatment group.

The medicaments according to Formulation Examples 1 to 18, applied as a spot-on at a dosage of 0.1 ml/kg, were found to be highly effective against *Rhipicefalus sanguineus*.

C. Activity Against Fleas and Ticks Over a Period of 6 Weeks

The activity of the compositions according to the invention against fleas and ticks was tested over a period of 6 weeks. The test was carried out analogously to the description given under items A and B.

TABLE 1

Activity of the composition according to Example 10 against fleas and ticks

| Number of the study | Design of the study/application volume 0.1 ml/kg | Activity against fleas (geo. mean)/ Activity against ticks (geo. mean) 1-2 days after treatment | Activity against fleas (geo. mean)/ Activity against ticks (geo. mean) 1 week after treatment | Activity against fleas (geo. mean)/ Activity against ticks (geo. mean) 2 weeks after treatment | Activity against fleas (geo. mean)/ Activity against ticks (geo. mean) 3 weeks after treatment |
|---|---|---|---|---|---|
| 1 | *Ctenocephalides felis/ Rhipicephalus sanguineus* | 100%/87.2% | 100%/89.9% | 100%/89.9% | 95.3%/97.6% |
| 2 | *Ctenocephalides felis/ Amblyomma americanum* | 100%/38.9% | 100%/100% | 100%/100% | 99.7%/100% |
| 3 | *Ctenocephalides felis/ Rhipicephalus sanguineus* | 100%/67.0% | 100%/95.9% | 99.8%/96.8% | 98.9%/94.1% |

| Number of the study | Design of the study/application volume 0.1 ml/kg | Activity against fleas (geo. mean)/ Activity against ticks (geo. mean) 4 weeks after treatment | Activity against fleas (geo. mean)/ Activity against ticks (geo. mean) 5 weeks after treatment | Activity against fleas (geo. mean)/ Activity against ticks (geo. mean) 6 weeks after treatment |
|---|---|---|---|---|
| 1 | *Ctenocephalides felis/ Rhipicephalus sanguineus* | 95.9%/91.4% | 90.6%/85.5% | 92.3%/83.6% |
| 2 | *Ctenocephalides felis/ Amblyomma americanum* | 99.0%/50.0% | 96.3%/92.8% | 99.0%/50.0% |
| 3 | *Ctenocephalides felis/ Rhipicephalus sanguineus* | 94.5%/85.0% | 68.1%/80.0% | |

The invention claimed is:

1. A composition for controlling parasites on an animal comprising:
   a. from about 35% to about 60% by weight of permethrin;
   b. from about 2.5% to about 12.5% by weight of imidacloprid or an imidacloprid analog;
   c. from about 27.5% to about 62.5% by weight of N-methylpyrrolidone;
   d. from 0% to about 5% by weight of water;
   e. from 0% to about 0.5% by weight of phenolic antioxidants; and
   f. from 0% to about 0.5% by weight of at least one organic acid.

2. The composition of claim 1, further comprising from about 2.5% to about 10% by weight of at least one cosolvent.

3. The composition of claim 1, wherein said parasite is selected from the group consisting of fleas, ticks and both fleas and ticks and wherein said animal is warm-blooded.

4. The composition of claim 3, wherein said animal is a dog.

* * * * *

(12) EX PARTE REEXAMINATION CERTIFICATE (9491st)
United States Patent
Sirinyan et al.

(10) Number: US 7,728,011 C1
(45) Certificate Issued: *Jan. 24, 2013

(54) DERMALLY APPLICABLE LIQUID FORMULATIONS FOR CONTROLLING PARASITIC INSECTS ON ANIMALS

(75) Inventors: Kirkor Sirinyan, Bergisch Gladbach (DE); Hubert Dorn, Wuppertal (DE); Martin Gilges, Cologne (DE); Olaf Hansen, Leichlingen (DE)

(73) Assignee: Bayer Animal Health GmbH, Leverkusen (DE)

Reexamination Request:
No. 90/011,677, May 6, 2011

Reexamination Certificate for:
Patent No.: 7,728,011
Issued: Jun. 1, 2010
Appl. No.: 10/682,127
Filed: Oct. 9, 2003

(*) Notice: This patent is subject to a terminal disclaimer.

Related U.S. Application Data

(63) Continuation of application No. PCT/EP02/03619, filed on Apr. 2, 2002.

(51) Int. Cl.
*A01N 43/40* (2006.01)

(52) U.S. Cl. .......... 514/341; 424/405; 514/351; 514/531

(58) Field of Classification Search .................. None
See application file for complete search history.

(56) References Cited

To view the complete listing of prior art documents cited during the proceeding for Reexamination Control Number 90/011,677, please refer to the USPTO's public Patent Application Information Retrieval (PAIR) system under the Display References tab.

*Primary Examiner* — Bruce Campell

(57) ABSTRACT

The present invention relates to novel skin-friendly dermally applicable liquid formulations comprising permethrin and agonists or antagonists of nicotinic acetylcholine receptors of insects for controlling parasitic insects on animals.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-4 is confirmed.

New claims 5-6 are added and determined to be patentable.

*5. A homogenous spot-on or pour-on composition active against parasitic insects comprising:*
  *a. 35% to 60% by weight of permethrin;*
  *b. 5% to 12.5% by weight of imidacloprid or an analogue thereof;*
  *c. 27.5% to 62.5% by weight of N-methylpyrrolidone;*
  *d. from 0% to about 5% by weight of water;*
  *e. from 0% to about 0.5% by weight of phenolic antioxidants; and*
  *f. from 0% to about 0.5% by weight of at least one organic acid.*

*6. A homogenous spot-on or pour-on composition active against parasitic insects comprising:*
  *a. 35% to 55% by weight of permethrin;*
  *b. 7.5% to 10% by weight of imidacloprid or an analogue thereof;*
  *c. 35% to 50% by weight of N-methylpyrrolidone;*
  *d. from 0% to about 5% by weight of water;*
  *e. from 0% to about 0.5% by weight of phenolic antioxidants; and*
  *f. from 0% to about 0.5% by weight of at least one organic acid.*

\* \* \* \* \*